United States Patent [19]
Papaioannou et al.

[11] Patent Number: 5,807,262
[45] Date of Patent: Sep. 15, 1998

[54] DEVICE FOR LOCALIZING AN OBJECT IN A TURBID MEDIUM USING A MODULATED LIGHT SOURCE

[75] Inventors: Dimitrios Papaioannou; Gert W. 't Hooft, both of Eindhoven, Netherlands

[73] Assignee: U.S. Philips Corporation, New York, N.Y.

[21] Appl. No.: 770,031

[22] Filed: Dec. 19, 1996

[30] Foreign Application Priority Data

Dec. 22, 1995 [EP] European Pat. Off. .............. 95203607

[51] Int. Cl.[6] ..................................................... A61B 5/05
[52] U.S. Cl. .......................... 600/473; 600/476; 356/345
[58] Field of Search .................................. 128/664, 665, 128/633; 250/341.1, 339.12; 356/345, 39, 40, 41; 600/473, 476, 310

[56] References Cited

U.S. PATENT DOCUMENTS

| | | | |
|---|---|---|---|
| 5,203,339 | 4/1993 | Knuttel | 128/665 |
| 5,309,907 | 5/1994 | Fang et al. | 128/633 |
| 5,441,054 | 8/1995 | Tsuchiya | 128/665 |
| 5,553,614 | 9/1996 | Chance | 128/633 |
| 5,582,169 | 12/1996 | Oda et al. | 128/633 |

FOREIGN PATENT DOCUMENTS

WO9418545   8/1994   WIPO .

*Primary Examiner*—William E. Kamm
*Assistant Examiner*—Eleni Mantis Mercader
*Attorney, Agent, or Firm*—Jack D. Slobod

[57] ABSTRACT

A device (700) for localizing an object (726) in a turbid medium (710) includes one light source (722) and two detectors (723,724), being symmetrically situated relatively to the light source (722), around a turbid medium (710). By applying a pulse modulated light source an optimal frequency could be determined to perform measurement at optimal sensitivity of the system. To enable a fast scanning system that could be used in for example mammography, a plurality of light sources (1209) and plurality of detectors (1201 to 1208) could be used. A processing system (105) selects then repetitively one light source (1209) and a different detector pairs, that are symmetrically situated relatively towards the light source (1209). Another embodiment that could be used in the mammography includes rotating mirrors (1303,1309) to scan a measuring space (1304) adapted to contains an object (1305), for example a human breast. The detector used in this embodiment includes a streak camera (1313). A lens (1308) and one of the rotating mirrors (1309) images two exit locations (1306,1307) of the measuring space (1304) that are symmetrically situated toward an entrance location (1303) of the measuring space on the entrance slit (1312) of the streak camera (1313). The output-image (1315) of the streak camera (1313) is imaged by an image pick-up device (1316) and processed by a processing system (1318) to obtain an image of the object in the measuring space (1304). A monitor (1319) displays the obtained image.

20 Claims, 7 Drawing Sheets

DEVICE FOR LOCALIZING AN OBJECT IN A TURBID MEDIUM USING A MODULATED LIGHT SOURCE

BACKGROUND OF THE INVENTION

1. Field of the Invention

The invention relates to a device for localizing an object in a turbid medium, including:

- a light source for irradiating the turbid medium by means of modulated light having a modulation frequency,
- a detector for generating a detector signal from the modulated light emanating from the turbid medium, and
- a processing unit for determining optical parameters of the turbid medium from the detector signal.

2. Description of the Related Art

A device of this kind is known from the article "Refraction of Diffuse Photon Density Waves" by M. A. O'Leary et al, published in Physical Review Letters, Vol. 69, No. 19, November 1992. The known device is used for the examination of a turbid medium, for example biological tissue. The turbid medium to be examined, containing a hidden object, is arranged between the light source and the detector. Subsequently, intensity-modulated light is generated by the light source and is applied to the turbid medium. The propagation of the intensity-modulated light in the turbid medium between the light source and the detector can be described by the propagation of a photon density wave in the turbid medium. The detector converts light emanating from the turbid medium into a detector signal. Optical parameters of the turbid medium, for example the absorption coefficient and the scattering coefficient, are determined from the amplitude and the phase of the detector signal. The presence and magnitude of an object in the turbid medium can be established on the basis of the differences in the absorption and scattering coefficients found by scanning by means of the light source and the detector. The known device can be used, for example, for the medical diagnostics, notably for mammography for localizing of tumors in breast tissue.

It is a drawback of the known device that during the execution of a measurement on the turbid medium it is not known whether or not measurement is being carried out with the optimum sensitivity.

SUMMARY OF THE INVENTION

It is inter alia an object of the invention to provide a device which offers a result obtained with optimum sensitivity of the device. To this end, the device in accordance with the invention is characterized in that it comprises means for the pulsed modulation of the light. The optimum sensitivity of the device is determined by the wavelength of the photon density wave, the sensitivity of the detector, and the distance between the light source and the detector. This step introduces a superposition of photon density waves with different wavelengths into the turbid medium with associated frequencies which are in a range from the repetition frequency of the pulse up to the limit frequency of the detector. After execution of a measurement, the results associated with the optimum sensitivity can be selected from the measured data.

An embodiment of the device in accordance with the invention is characterized in that the device comprises a second, light source for irradiating the turbid medium by means of modulated light, the modulation of the modulated light of the second light source being the same as, but shifted in time, with respect to the modulation of the modulated light of the first light source. This step enhances the sensitivity for the detection of the object in the turbid medium. The second light source generates a second photon density wave in the turbid medium. For a homogeneous turbid medium it now holds that a pronounced phase transition occurs in the detector signal in a detector position along the symmetry axis between the two light sources. If the symmetry is disturbed by the presence of an object in the turbid medium, the position in which this phase transition is observed is shifted. The position of the object in the turbid medium can be determined by scanning the turbid medium in two orthogonal directions relative to the symmetry axis by means of the light sources and detector.

The use of intensity pulse modulated light sources introduces a superposition of photon density waves with different wavelengths from the light sources into the turbid medium. By adjustment of the magnitude of the time shift $\Delta T$ of the second light source relative to the first light source, two photon density waves which have been shifted 180° relative to one another are chosen from the superpositions. In order to determine the result with inter alia optimum sensitivity, a series of measurements is carried out with different time shifts $\Delta T$, the turbid medium thus being scanned and the time responses of the detector signals of the series of measurements being determined. Subsequently, frequency spectra are determined from the time responses. Due to the time shift $\Delta T$, the frequency spectra contain relative minimum values at the frequency $1/(2\Delta T)$ and odd harmonics thereof. The range in which the time shift $\Delta T$ can be chosen is, for example the range between 1 ns and 50 ns. After completion of the measurements, a set of frequency spectra will be available wherefrom the measurement result with optimum frequency is determined.

A device comprising two light sources and a detector is known from WO 93/25145. The known device also utilizes two photon density waves which are generated by two light sources, the amplitude modulation of the intensity of the first light source being in phase opposition relative to amplitude modulation of the second light source. However, the known device utilizes only one sinusoidal modulation frequency for the modulation of the intensity of the light sources, so that photon density waves of only a single frequency occur in the turbid medium.

A further embodiment of the device in accordance with the invention is characterized in that, in addition to said first detector, the device comprises, a second detector for generating a second detector signal from the modulated light emanating from the turbid medium, and that the processing unit is arranged to determine amplitude and/or phase of a difference signal of the first and the second detector signal. This step offers the advantage that the sensitivity of this embodiment is higher than in the case of a measurement utilizing two light sources and a single detector. This because in the case of measurement by means of a single light source and two detectors, the alternating voltage component in the difference signal between the two detectors is much larger than the alternating voltage component in the detector signal in the case of a measurement utilizing two light sources and a single detector.

The ratio of the alternating voltage component to the direct voltage component of the detector signal in the case of a measurement carried out by means of two light sources and a detector is approximately 1:1000, whereas the ratio of the alternating voltage component to the direct voltage component in the case of a measurement by means of one light source and two detectors is approximately 1:2. Also for other types of amplitude modulation of the intensity of the light source a combination applying a single light source and two detectors is far more sensitive then a combination of two light sources and one detector, for example a sinusoidal amplitude modulation. Measurement is then carried out on a turbid medium in the same way as the measurement utilizing two light sources and one detector. To this end, a photon density wave is generated by means of the light source. If the light source is symmetrically arranged relative to the two detectors, in the case of a homogeneous turbid medium the direct voltage component as well as the alternating voltage component of the difference signal will be substantially zero for a position on the symmetry axis. During the scanning of the turbid medium with the source and detectors in a direction orthogonal to the symmetry axis of the light source and the two detectors, a local maximum occurs in the direct voltage component as well as in the alternating voltage component of the difference signal between the two detector if the hidden object is situated between one of the two detectors and the light source. The enhanced detection sensitivity also enables a higher resolution to be achieved by using a higher frequency of the photon density waves. A device with one light source and two detectors is known, per se, from WO 93/25145, however no details are disclosed in that patent application.

A further embodiment of the device in accordance with the invention is characterized in that it comprises a plurality of detectors which are arranged in one plane, the first detector and the second detector being selected from the detectors by the processing unit. The advantage of this step resides in the fact that the light emanating from the turbid medium can be detected in successive, different detector positions without displacement of the detectors being required.

Another embodiment of the device in accordance with the invention is characterized in that the device comprises four detectors which are arranged in a square, that the light source is arranged substantially at equal distances from the detectors, and that a measuring space capable of containing the turbid medium is situated between the light source and the detectors. The advantage of this step resides in the fact that the scanning of the turbid medium by means of this so-called quadrant detector is faster, because per displacement of the detectors a result can be measured in two orthogonal directions with respect to the symmetry axis of the light source and the four detectors.

Another embodiment of the device in accordance with the invention is characterized in that the detectors are arranged according to a regular polygon which encloses a measuring space in which the turbid medium can be provided, the light source being arranged substantially halfway between two adjacent detectors, the processing unit arranged to select two detectors which are symmetrically situated relative to the light source. As a result of this step, in which the detectors and the light source are arranged on a support which encloses the measuring space, the light emanating from a turbid medium can be measured in one plane, it being possible to measure the difference signals pertaining to all detector pairs which are symmetrically situated relative to the light source by mechanical adjustment of the light source relative to the turbid medium.

A further embodiment of the device in accordance with the invention is characterized in that it comprises a plurality of equidistant light sources which are arranged substantially halfway between two adjacent detectors on the polygon, the processing unit being arranged to execute the following steps repetitively:

selecting one of the light sources, selecting for every selected light source, several times, different detector pairs, which are symmetrically situated relative to the selected light source, measuring the amplitude and/or the phase from a combination of detector signals from the selected detectors.

When mounting a plurality of detectors as well as a plurality of light sources are mounted on the same support, enclosing the measuring space, the turbid medium can be irradiated from different directions and at the same time the light emanating from the turbid medium can be detected in different directions. Consequently, the support can remain in a fixed position around the turbid medium, so that measurements can be carried out faster.

Another embodiment of the device in accordance with the invention is characterized in that the detectors are arranged on a single straight. The detectors are thus arranged to one side of the turbid medium and opposite a light source.

Another embodiment of the device in accordance with the invention is characterized in that the detectors are coupled to the entrance slit of a streak camera either directly or via a optical system. The optical coupling of exit ports of the measuring space to the entrance slit of a streak camera enables simultaneous measurement of the time response of respective exit ports in different locations.

A further embodiment of the device in accordance with the invention is characterized in that the device comprises mechanical and/or optical means for scanning the measuring space. This step enables scanning of the measuring space while according to a first possibility where the light source and the detector are mounted on a support, the support is moved along the measuring space by means of a mechanical device. According to a second possibility, the light source and the detector are arranged in a fixed position and the measuring space is scanned by means of inter alia rotating mirrors.

These and other aspects of the invention will be apparent from and elucidated with reference to the embodiments described hereinafter.

DESCRIPTION OF THE PREFERRED EMBODIMENTS

Figure 1:
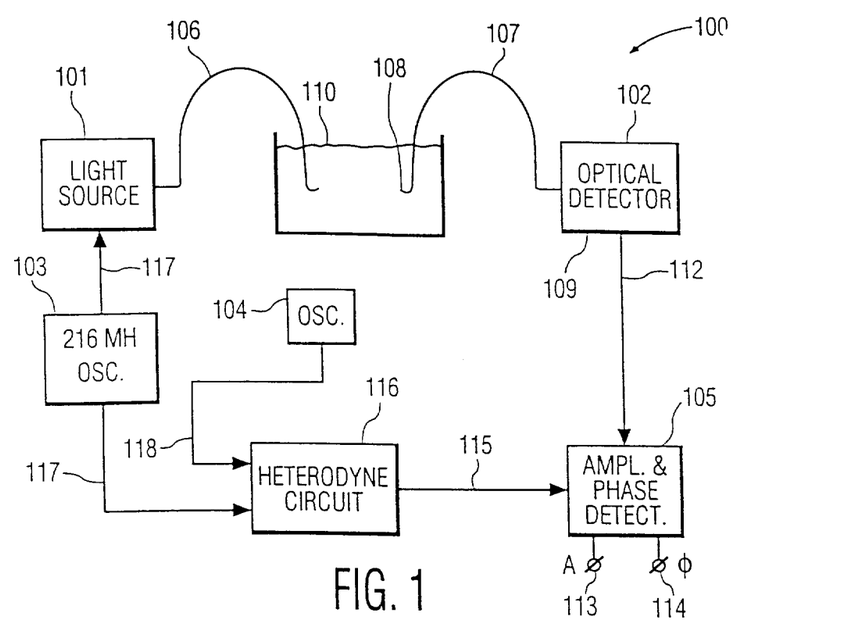
FIG. 1 shows a device comprising a light source and a detector.

FIG. 1 shows a known device 100, comprising a light source 101 and a detector 102. This device is known from the cited article "Refraction of Diffuse Photon Density Waves" by M. A. O'Leary et al. The known device also comprises a first oscillator 103, a second oscillator 104, and an amplitude and phase detector 105. The first oscillator 103 generates a control signal 117 of, for example 216 MHz for intensity modulation of the light source 101. The light source is, for example a laser diode having an optical wavelength of, for example 800 nm. A first optical conductor 106 conducts the light generated by the light source 101 to a turbid medium 110. The turbid medium 110 is, for example a container 111 containing an Intralipid solution. A second optical conductor 107, whose first end 108 is arranged in a detector position in the turbid medium 110 and whose second end 109 is coupled to an optical detector 102, guides a part of the light from the turbid medium 110 to the detector 102. Under the influence of the incident light, the detector 102 generates a detector signal 112. The amplitude and phase detector 105 determines an amplitude 113 and a phase 114 of said detector signal 112. To this end, the amplitude and phase detector 105 requires a reference signal 115 which is generated by means of a heterodyne circuit 116. The heterodyne circuit 116 determines the difference signal, being the reference signal 115, between the control signal 117 and a second signal 118 which originates from the second oscillator 104. The frequency $f_1$ of the first oscillator 103 amounts to, for example 216 MHz. The frequency of the second oscillator $f_2$ equals the sum of the frequency $f_1$ of the control signal and a small difference frequency $\Delta f$ which amounts to, for example 1 kHz.

Scalar, damped travelling waves, referred to as photon density waves, are used to the describe the behavior of the intensity of the modulated light in the turbid medium. An object present in the turbid medium between the light source and the detector causes a disturbance of the wave front of the photon density wave, and hence a deviation in the detected phase and amplitude. Furthermore, the amplitude of the detector signal is dependent on the distance between the light source and the detector and also on the absorption coefficient and the scattering coefficient of the turbid medium.

In order to enhance the sensitivity for the detection of hidden objects in the turbid medium, use is made of a second light source whose intensity modulation is in phase opposition with respect to the first light source. It generates a second photon density wave in the turbid medium and pronounced phase transition occurs in the turbid medium. This device is known from the cited patent application WO 93/25145. This known device will be described in detail hereinafter with reference to FIG. 2.

Figure 2:
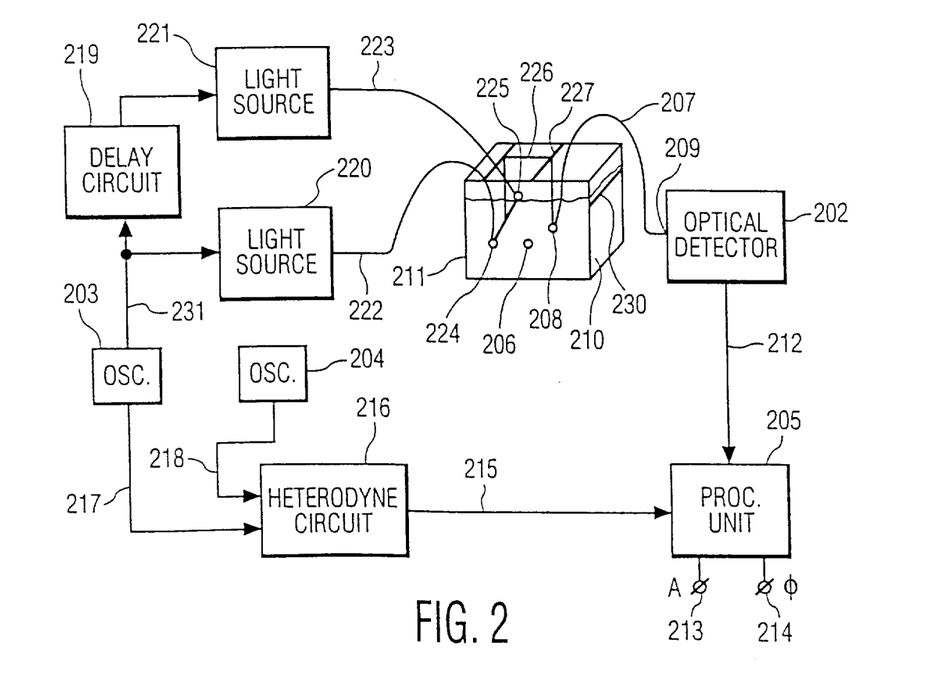
FIG. 2 shows a device comprising two light sources and one detector.

FIG. 2 shows a known device 200 which comprises a first light source 220, a second light source 221 and a detector aperture 208. The first light source 220 generates intensity-modulated light by means of a first modulation signal 231 of frequency $f_1$ which originates from an oscillator 203. An optical conductor 222, having a first end coupled to the light source 220 and a second end 224 connected to a mechanical scanning device 226 conducts the light into the turbid medium 210. A second optical conductor 223, having a end which is coupled to the light source 221 and a second end 225 which is also connected to the mechanical scanning device 226, conducts the light of the second light source 221 into the turbid medium 210. The second light source 221 is intensity modulated by a modulation signal 231 whose phase has been reversed with respect to the first modulation signal 231 by a delay circuit 219. As a result, the modulation of the first light source 220 is also in phase opposition with respect to the modulation of the second light source 221. A part of the light from the turbid medium is detected via a detector aperture 208. The detector aperture 208 is arranged on the mechanical scanning device 226 so as to be symmetrical with respect to the ends 224,225 of the optical conductors 222, 223. The detector aperture 208 is formed by a first end of a third optical conductor 207 whose other end 209 is coupled to an optical detector 202. The optical detector 202 generates a detector signal 212 which is, for example proportional to the light emanating from the turbid medium 210 via the optical conductor 207. A processing unit 205 determines an amplitude 213 and a phase 214 from the detector signal 212 using reference signal 215 produced by heterodyne circuit 216 in response to the signal from oscillator 203 and from a second oscillator 204. The distance between the ends (224,225) of the two optical conductors 222, 223 amounts to, for example 10 mm in the present device and the distance between the central point between the two ends 224, 225 of the optical conductors 222, 223 and the detector aperture 208 amounts to, for example 50 mm. The turbid medium 110 is, for example an Intralipid solution in a container 211. The scattering coefficient $\mu s$ of the turbid medium amounts to 1.0 $mm^{-1}$ and the absorption coefficient $\mu_a$ amounts to 0.001 $mm^{-1}$. Furthermore, in the homogeneous turbid medium a hidden object 206 having a radius of 5 mm is present in a position in the center of the container 211. The scattering coefficient of the object 206 amounts to 1.0 $mm^{-1}$ and the absorption coefficient of the object 206 is 0.01 $mm^{-1}$.

Upon execution of measurements wherein the source and the detectors are placed at a number of positions along a line 227 extending orthogonally with respect to the symmetry axis of the light sources and the detector the amplitude and the phase are measured in dependence on the position of the detector relative to the center of one side 230 of the container. The amplitude characteristic and the phase characteristic of the detector signal are shown in the FIGS. 3 and 4, respectively.

Figure 3:
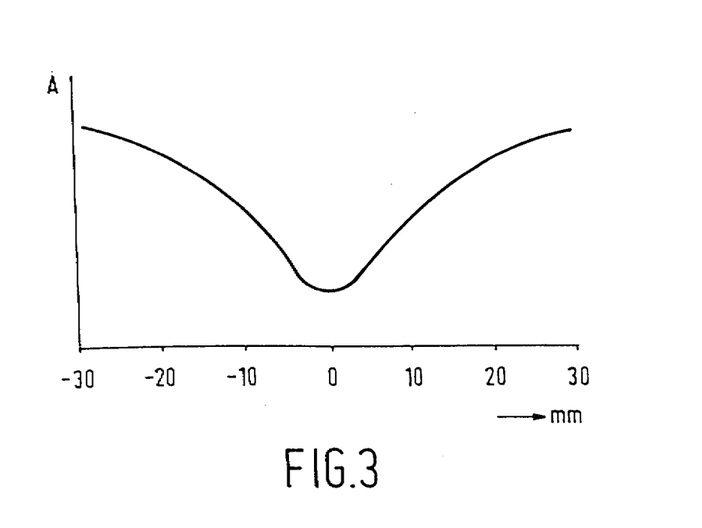
FIG. 3 shows the known measuring characteristic of the amplitude of a detector signal due to the sinusoidal modulated light of two light sources.

FIG. 3 shows an amplitude characteristic of the detector signal after execution of such a measurement. The amplitude characteristic exhibits a minimum on the symmetry axis.

Figure 4:
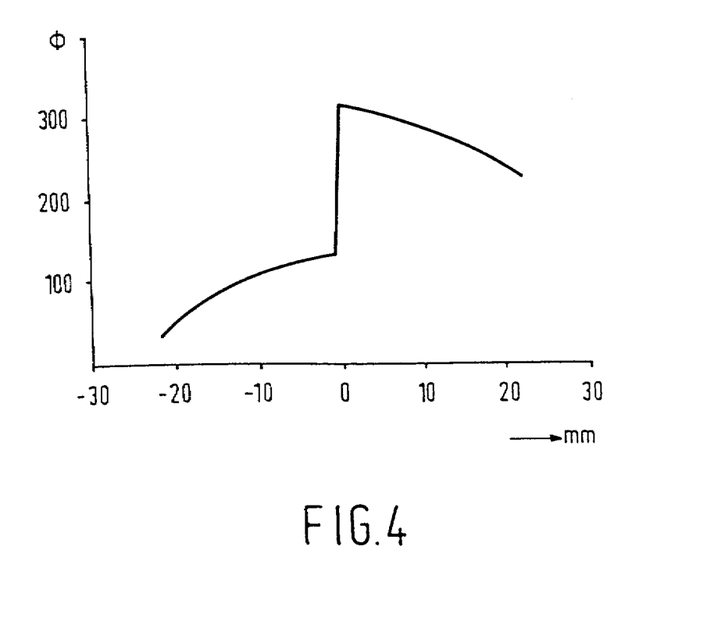
FIG. 4 shows the known measuring characteristic of the phase of a detector signal due to the sinusoidally modulated light of two light sources.

FIG. 4 shows a phase characteristic of the detector signal. The phase characteristic exhibits a maximum phase change in a position 0 which corresponds to the middle of the side 230 of the container.

In order to determine a measured result at inter alia the optimum frequency of the measuring device, in accordance with the invention an adjustable series of frequencies of the intensity modulation is introduced into the turbid medium by pulsed modulation of the intensity of the light sources. These measurements will be described in detail with reference to the measuring set-up shown in FIG. 5.

Figure 5:
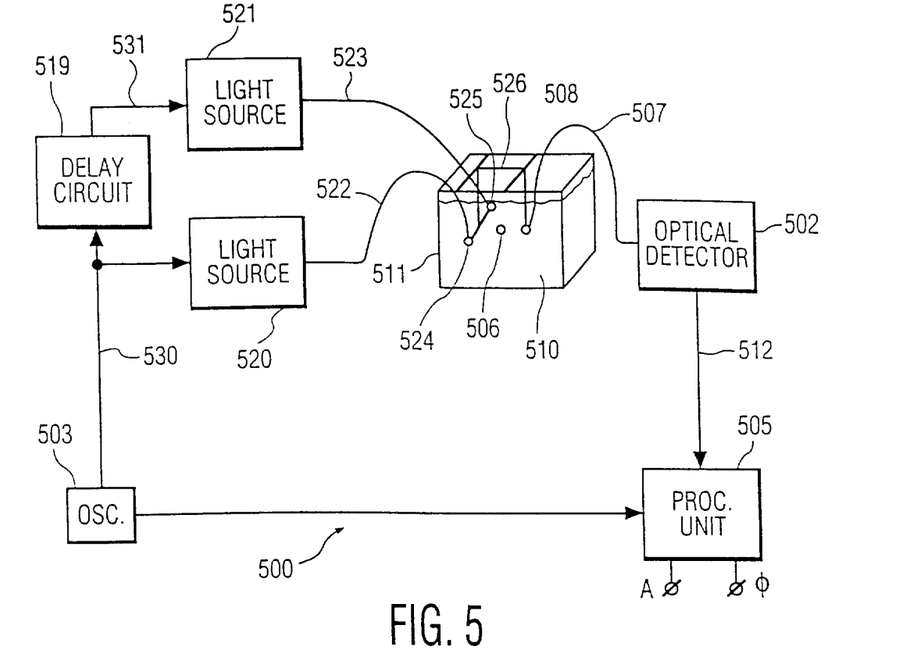
FIG. 5 shows a second device for measuring intensity pulse modulated light.

FIG. 5 shows a measuring set-up for executing measurements by means of pulse modulation. The measuring set-up is substantially identical to the set-up described with reference to FIG. 2. However, an oscillator 503 now generates a pulse modulation signal 530. The pulse modulation signal 530 contains a pulse of a length of, for example 150 femtoseconds. The repetition frequency is, for example 216 MHz. The pulse modulation signal 530 is applied to a first light source 520. The first light source 520 generates pulsed, intensity-modulated light. A second modulation signal 531 is used from the pulse modulation signal 530 by means of the delay circuit 519. The second pulse modulation signal 531 serves for intensity modulation of the second light source 221. The intensity modulation of the second light source 521 is the same as that of the first light source 520, has been shifted a delay period $\Delta T$ but with respect thereto. The frequency for which the modulation of two light sources are in phase opposition can be selected by variation of the delay time $\Delta T$. This frequency is then determined as $$\frac{1}{2\Delta T}.$$

Another possibility to delay the intensity modulation of one light source relative to the other light source is to apply an optical beam splitter in order to create two light source and to create an optical path difference when the light is conducted in the turbid medium.

Figure 6:
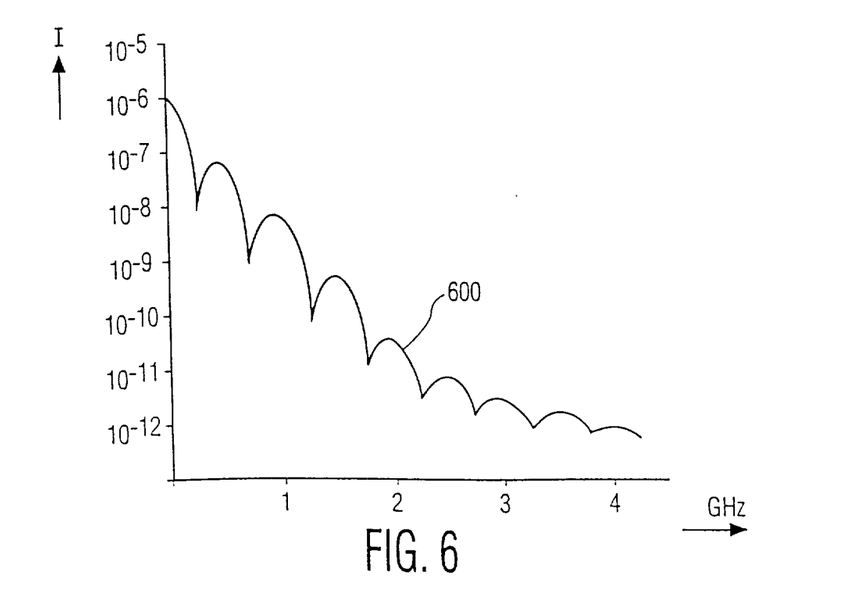
FIG. 6 shows the frequency response of the detector signal due to the measurement of pulse modulated light.

In accordance with the invention, the measurements are determined at the optimum frequency by analysis of the detector signal. To this end, a processing unit 505 determines a frequency spectrum of the time response of the detector signal 512 of the detector 502. FIG. 6 shows a frequency spectrum 600 of the detector signal 512 obtained by means of the described set-up comprising two light sources and a single detector at a distance of 50 mm. The distance between the two light sources is typically 10 mm. This frequency spectrum exhibits local minima at the repetition frequency f and odd harmonic of this repetition frequency. The frequency spectra for different delay times $\Delta T$ can be obtained by performing a number of measurements for different delay times $\Delta T$ in a range between about 0.5 and 5 ns. The measured results with an optimum sensitivity are determined from the frequency spectra.

The sensitivity for the detection of objects can be improved in accordance with the invention by utilizing a measuring device comprising one light source and two detectors. This device will be described with reference to FIG. 7.

Figure 7:
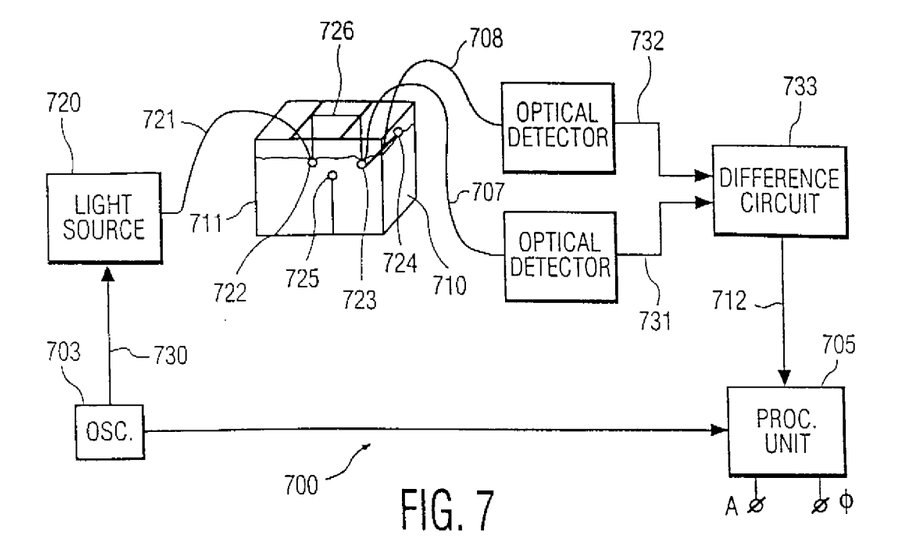
FIG. 7 shows a device comprising one light source and two detectors.
Figure 8:
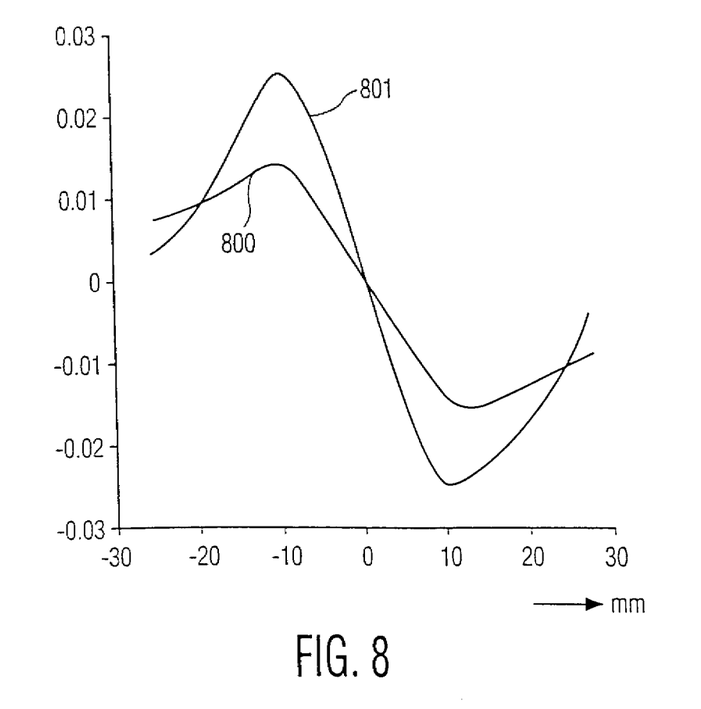
FIG. 8 shows a direct voltage component and an alternating voltage component of the difference signal between two detectors.

FIG. 7 shows a device which comprises a light source 720, a first detector 701 and a second detector 702. The operating of this devices is equivalent of the embodiment of FIG. 6 because the light transport in the turbid medium is a linear phenomenon and can be described by photon density waves and the associated diffusion equation is linear. Therefore not only the intensity contribution from different light sources may be added, but it also holds that the light paths are reversible and consequently, the light sources and the detectors can be interchanged. The ends 723,724 of optical conductors 707,708 are arranged in the turbid medium 710 on a mechanical scanning device 726. A first end 722 of a first optical conductor 721 is arranged in the turbid medium 710 on the mechanical scanning device 726 so as to be symmetrical relative to the ends 723, 724 of the optical conductors 707,708. The oscillator 703 generates a sinusoidal signal. The light source 720 is intensity-modulated by this sinusoidal signal. The first optical conductor 721 conducts said intensity-modulated light into the turbid medium 710. The second optical conductor 707, whose first end 723 is situated in a first position in the turbid medium 710 whereas its other end is coupled to a first detector 701, conducts a part of the light from the turbid medium 710 to said first detector 701. A third optical conductor 708, whose first end 724 is situated in a second position in the turbid medium 710 and whose other end is coupled to a second detector 702, conducts another part of the light from the turbid medium 710 to said second detector 702. The first detector 701 produces a first detector signal 731 and the second detector 702 produces a second detector signal 732. Subsequently, a difference circuit 733 determines the difference signal 712 between the two detector signals 731, 732. The processing unit 705 determines a DC component and an AC component from said difference signal. In the device described herein the distance between light source and detector is 50 mm, the distance between the detectors is 10 mm. Furthermore, an object is arranged at the centre of the container 711, containing the turbid medium, in a position 0 along an axis orthogonal to the symmetry axis of the combination formed by the light source and the detectors. Absorbing and scattering coefficients of the turbid medium and the object are equal to those used in the description of FIG. 2. FIG. 8 shows a graph with the DC and AC components of the difference signal between the two detectors as a function of the light source detector position as measured with this embodiment.

A first curve 800 in FIG. 8 denotes the variation of the DC component as a function of the position of the scanning line. A second curve 801 represents the variation of the AC component as a function of the position along the scanning line. The ratio of the DC component to the AC component in the difference signal between two detectors is approximately 2:1, whereas the ratio of the DC component to the AC component in the detector signal amounts to only approximately 1000:1 when measured utilizing two light sources and a detector. The advantage of the device comprising two detectors and one light source consists in that the DC component and the AC component of the difference signal between the first and the second detector signal now exhibits variations of the order of magnitude of a few percents during the measurement. Furthermore, the relative maxima of the AC component are larger and the steepness around the 0 of the characteristic is greater.

In order to carry out a measurement at inter alia the optimum frequency in a device comprising one light source and two detectors in accordance with the invention, pulsed intensity-modulated light is generated by the light source 720. An optical conductor 721 conducts the light produced into the turbid medium 710 in a position on the symmetry axis between the two ends 723, 724 of the optical conductors 707,708. Subsequently, the turbid medium 710 is scanned in a direction orthogonal to the symmetry axis and parallel to a line trough both detectors by means of the mechanical scanning device 726. The time response of the difference signal between the two detector signals is determined for each measuring position. Here the time response is the amplitude of the difference signal as a function of time passed after each rising edge of a pulse of the modulation signal. The time responses measured are represented by three-dimensional characteristic as shown in FIG. 9.

Figure 9:
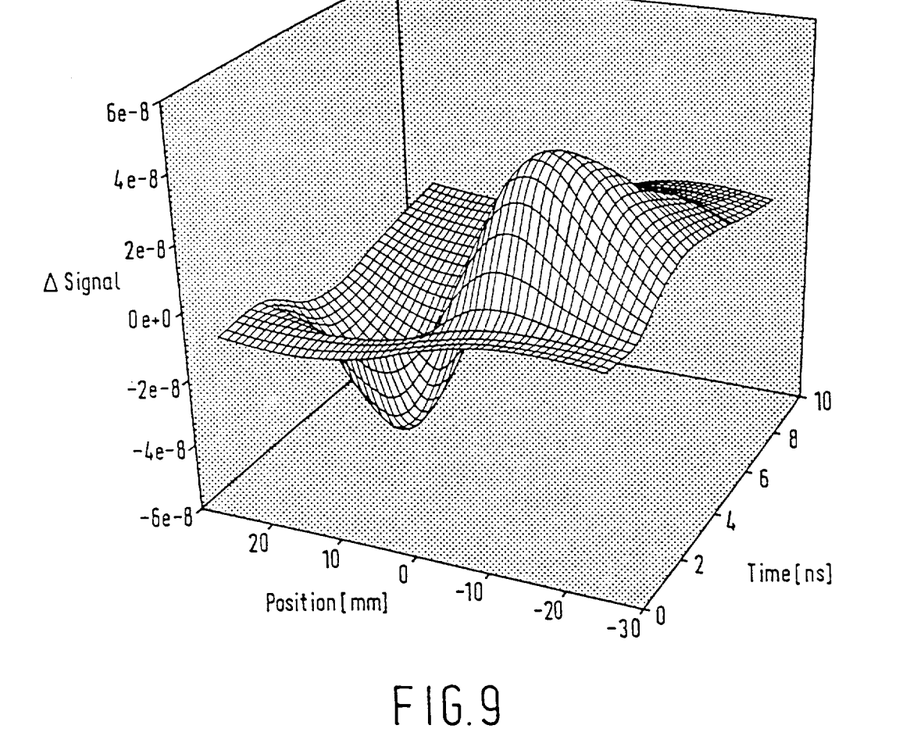
FIG. 9 shows the pulse responses of a series measurement using intensity pulse modulated light.

FIG. 9 shows the time response characteristic. On a first axis the location of the light source/detector combination is plotted along a line extending orthogonally to the symmetry axis of the light source/detector combination; on a second axis the time elapsing after the application of the pulse is plotted and the amplitude of the AC component of the difference signal is plotted on a third axis. The pulse length of the light source 720 during the execution of the measurements amounts to approximately 150 femtoseconds, but other, higher values are also feasible, for example 1 picosecond. The characteristic of FIG. 9 shows that the highest amplitude in the pulse response, i.e. the optimum sensitivity, is found for a time of about 4 nanoseconds. This time is dependent on the light source/detector distance and on the scattering coefficient of the turbid medium.

In order to carry out measurements on, for example breast tissue during mammography, inter alia two measuring set-ups could be used. A first set-up utilizes a quadrant detector whereas another set-up utilizes a multitude of detectors.

Figure 10:
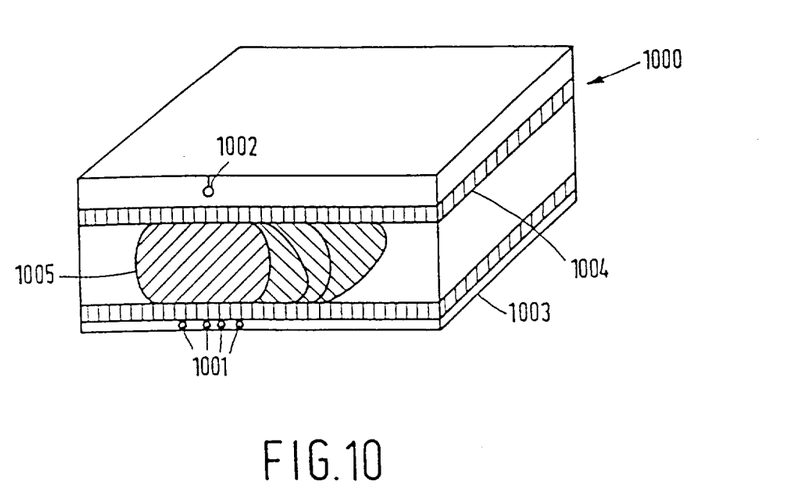
FIG. 10 shows a measuring device comprising a quadrant detector in accordance with the invention.

FIG. 10 shows a measuring space of a device in which a quadrant detector is used. The quadrant detector comprises four detectors 1001 which are arranged in a square on a mechanical scanning device 1003. A light source 1002 is arranged on the mechanical scanning device 1003 in a position on the symmetry axis through the centre of the square. Between the light source and the detectors there is formed a measuring space 1004 in which the turbid medium 1005, for example a breast of a patient, can be arranged. The measuring space with the quadrant detector can be used in combination with a set-up as described with reference to FIG. 7. Via the quadrant detector, per measuring position a first measurement can be performed in a first direction and a second measurement can be performed in a second direction which extends substantially perpendicularly to the first direction. By scanning the measuring space in two orthogonal directions by means of the quadrant detector and the light source, the difference signal between two detectors, each being selected in the same orthogonal direction, can be determined in any position. A deviation between the difference signal and a reference signal indicates a disturbance between the light source and the detectors. A two-dimensional projection image of the turbid medium and the object hidden therein can be derived from the disturbances.

In order to determine a measured result at the optimum frequency, in accordance with the invention use can be made of the pulsed, intensity-modulated light source.

Figure 11:
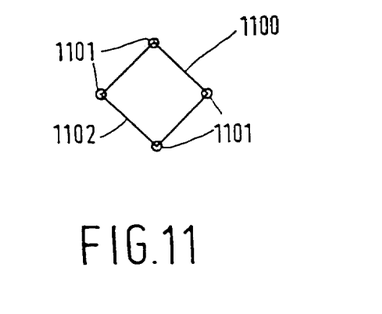
FIG. 11 shows a quadrant detector.

FIG. 11 shows a quadrant detector which comprises four detectors 1101 which are mounted in a square on a carrier 1102. Instead of a mechanical scanning device, use can be made of an optical scanning device, for example a measuring device comprising N detectors and a light source. Such a device will be described in detail hereinafter with reference to FIG. 12.

Figure 12:
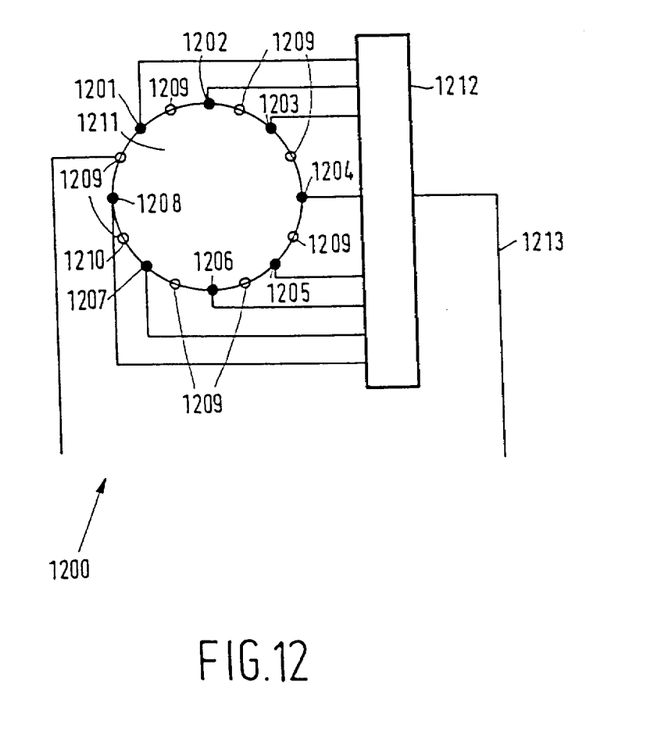
FIG. 12 shows a measuring device which comprises a light source and nine detectors.

FIG. 12 shows a device comprising N detectors and a light source, where N is an integer even number. For illustrative reasons in the Figure N is assumed to be equal to 8, being an integer even number. In a real experiment N could be, for example, 64. At the corner points of a regular polygon the detectors 1201 to 1208 are mounted on a carrier 1210 around a measuring space 1211 that contains he turbid medium. The light source 1209 is mounted substantially in the middle between the first detector 1201 and the eighth detector 1208 at the opposite side of the measuring space 1211. Via the selection unit 1213 the difference signal 1213 is selected from the four, N/2, detector pairs symmetrically situated with respect to the light source 1209 i.e. the pairs [1201, 1208], [1202, 1207], [1203, 1206], [1204, 1205]. A deviation in respect of the absorption or scattering coefficient is again determined on the basis of the difference signal 1213. In order to scan the plane containing the light source and the N detectors from different angles, the carrier 1210 with the light source 1209 and the detectors 1201 to 1208 is displaced or rotated with respect to the measuring space 1211. Another method of scanning the measuring space 1211 from different angles is the use of N light sources, each of which is arranged substantially halfway between two adjacent detectors. For each series of measurements a second selection unit then selects one of the N light sources 1209 and for the successive measurements within the series N/2 detector pairs which are symmetrically situated relative to the light source 1209 are selected by the first selection unit 1212.

In the described measuring set-ups amplitude-modulated laser diodes for generating light of fixed modulation frequency offer satisfactory results. The laser diode has a fixed wavelength in a range of between, for example 600 and 1000 nm. When time response measurements are performed, a short pulse laser can be used as the light source, for example a mode-locked or gain-switched semiconductor laser or a mode-locked Ti sapphire laser. Fast photodiodes (avalanche photodiodes) or photomultiplier tubes can be used as detectors. The time response from various locations can be simultaneously measured using a streak camera, by imaging the detector positions on the entrance slit by means of optical system, for example consisting of optical conductors, or by utilizing lenses and mirrors. A device utilizing a streak camera will be described in detail hereinafter with reference to FIG. 13.

Figure 13:
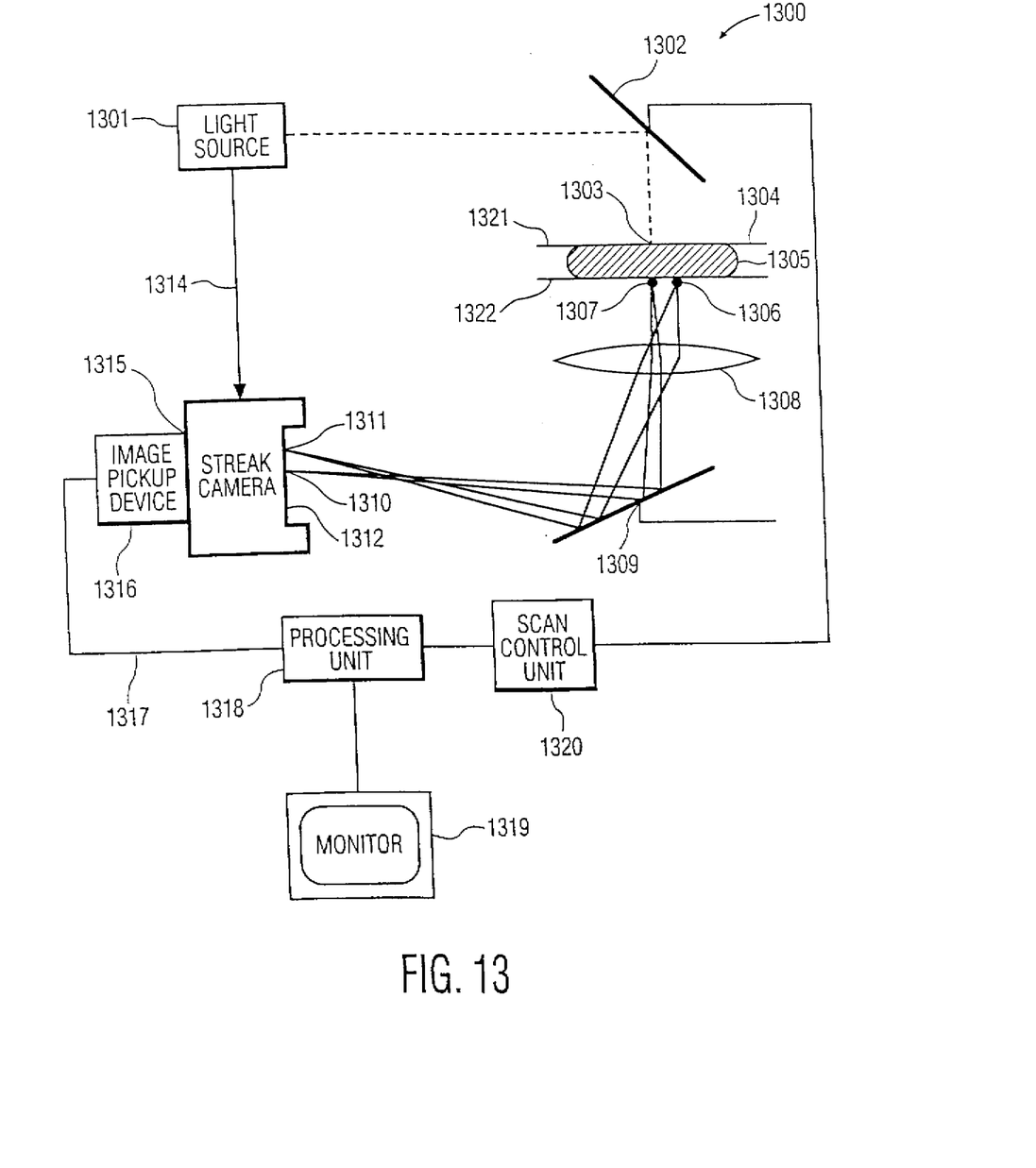
FIG. 13 shows a measuring device comprising a mechanical-optical scanning device and a streak camera.

FIG. 13 shows a device for measuring a turbid medium arranged in the measuring space. The device 1300 comprises a light source 1301 for generating pulsed, intensity-modulated light. A first rotating mirror 1302 applies the light emanating from the light source 1301 to different, successive entrance locations 1303 in the measuring space 1304. A turbid medium 1305 can be introduced into the measuring space 1304. The light emanating from two exit locations 1306, 1307, being symmetrically situated relative to the entrance location 1303, is imaged, by means of a lens 1308 and a second rotating mirror 1309 which moves in synchronism with the first rotating mirror 1302, onto two locations 1310, 1311 on an entrance slit 1312 of a streak camera 1313. The streak camera 1313 is time synchronously controlled by means of a trigger signal 1314 originating from the light source 1301 and time-synchronously determines the time response of the light incident on the two locations 1310, 1311 on the entrance slit. The time responses are imaged on an exit screen 1315. The exit screen 1315 of the streak camera 1313 is coupled to an image pick-up device 1316, for example a CCD camera. The image pick-up device 1316 converts the exit image of the streak camera 1313 into a video signal 1317. The processing unit 1318 determines the time response of the intensity in the measured location 1303 from the video signal 1317. During the execution of measurements, the measuring space 1304 is two-dimensionally scanned in an orthogonal grid of N×M points by means of the rotating mirrors 1302, 1309 and a scan control unit 1320. For the N×M Points the difference of the time response is measured in two successive exit locations 1306, 1307 of the measuring space 1304. Subsequently, a two-dimensional projection image of the turbid medium 1305 can be determined from the measured time responses. The projection image is then displayed on a monitor 1319.

It is remarked that because of the reversibility of the light paths between source and detectors, also more complicated embodiments of the invention could be realised by applying a plurality of light sources and a single detectors instead of a single light source and a plurality of detectors.

We claim:

1. A device for localizing an object in a turbid medium, comprising:
    a first light source for irradiating the turbid medium by means of modulated light having a modulation in the form of pulses having a duration and a repetition frequency,
    detector for generating a detector signal from modulated light emanating from the turbid medium, and a processing unit for determining optical parameters of the turbid medium from the detector signal, wherein the duration and repetition frequency of said pulses is chosen to introduce into the turbid medium a superposition of photon density waves with different frequencies including the repetition frequency and higher harmonics thereof.

2. A device as claimed in claim 1, further comprising a second light source for irradiating the turbid medium by means of modulated light, the modulation of the modulated light of the second light source being the same as but shifted in time with respect to the modulation of the modulated light of the first light source.

3. A device as claimed in claim 2, further comprising means for scanning a measuring space capable of containing the turbid medium.

4. A device as claimed in claim 1, further comprising means for scanning a measuring space capable of containing the turbid medium.

5. A device for localizing an object in a turbid medium comprising:

a light source for irradiating the turbid medium by means of modulated light having a modulation frequency, a first detector and a second detector for generating a first detector signal and a second detector signal, respectively, in response to modulated light emanating from the turbid medium, and processing means for determining optical parameters of the turbid medium, said processing means being arranged to determine the amplitude and the phase of a difference signal of the first and second detector signals.

6. A device as claimed in claim 5, further comprising a plurality of detectors, including said first and second detectors, which are arranged in one plane, said first and second detectors being selected from the plurality of detectors by the processing unit.

7. A device as claimed in claim 6, wherein the plurality of detectors comprises four detectors arranged in a square, the light source is arranged at substantially equal distances from the detectors, and a measuring space capable of containing the turbid medium is situated between the light source and the detectors.

8. A device as claimed in claim 7, further comprising means for scanning a measuring space capable of containing the turbid medium.

9. A device as claimed in claim 7, wherein the detectors are coupled to the entrance slit of a streak camera.

10. A device as claimed in claim 6, wherein the plurality of detectors are arranged according to a regular polygon which encloses a measuring space in which the turbid medium can be placed, the light source being arranged substantially halfway between two adjacent detectors, and the processing unit is arranged to select two detectors which are symmetrically situated relative to the light source.

11. A device as claimed in claim 10, further comprising means for scanning a measuring space capable of containing the turbid medium.

12. A device as claimed in claim 10, wherein the device comprises a plurality of equidistant light sources, including said first light source which are arranged substantially halfway between two adjacent detectors on the polygon, the processing unit being arranged to execute the following steps repetitively:

selecting one of the light sources, selecting for every selected light source, several times, different detector pairs which are symmetrically situated relative to the selected light source, and measuring amplitude and/or phase from a difference signal of detector signals from the selected detector pairs.

13. A device as claimed in claim 12, wherein the detectors are coupled to the entrance slit of a streak camera.

14. A device as claimed in claim 10, wherein the detectors are coupled to the entrance slit of a streak camera.

15. A device as claimed in claim 4, wherein the plurality of detectors are arranged on a single straight line.

16. A device as claimed in claim 15, wherein the detectors are coupled to the entrance slit of a streak camera.

17. A device as claimed in claim 6, wherein the detectors are coupled to the entrance slit of a streak camera.

18. A device as claimed in claim 6, further comprising means for scanning a measuring space capable of containing the turbid medium.

19. A device as claimed in claim 5, wherein the detectors are coupled to the entrance slit of a streak camera.

20. A device as claimed in claim 5, further comprising means for scanning a measuring space capable of containing the turbid medium.

* * * * *